US006277295B1

(12) United States Patent
Sarkar et al.

(10) Patent No.: US 6,277,295 B1
(45) Date of Patent: Aug. 21, 2001

(54) ETCHING ALUMINA CERAMICS

(75) Inventors: Nikhil Sarkar, New Orleans; Avishai Sadan, Metairie, both of LA (US)

(73) Assignee: Board of Supervisors of Louisiana State University and Argricultural and Mechanical College, Baton Rouge, LA (US)

( * ) Notice: Subject to any disclaimer, the term of this patent is extended or adjusted under 35 U.S.C. 154(b) by 0 days.

(21) Appl. No.: 09/298,500

(22) Filed: Apr. 23, 1999

(51) Int. Cl.$^7$ .................................................. B44C 1/022
(52) U.S. Cl. ............................................. 216/34; 216/102
(58) Field of Search ..................... 216/34, 102; 438/689, 438/754

(56) References Cited

U.S. PATENT DOCUMENTS

| 2,127,781 | * | 8/1938 | McKay ....................................... 41/42 |
| 3,894,337 | * | 7/1975 | Jones ................................. 30/346.54 |
| 4,221,824 | * | 9/1980 | Leonard et al. ........................ 427/27 |
| 4,647,477 | * | 3/1987 | DeLuca ................................... 427/98 |
| 4,781,792 | * | 11/1988 | Hogan ................................... 156/663 |
| 5,468,459 | * | 11/1995 | Tamhankar et al. .............. 423/240 S |
| 5,489,318 | * | 2/1996 | Erickson et al. ........................ 51/309 |
| 5,651,801 | * | 7/1997 | Monroe et al. ........................ 51/309 |
| 5,681,217 | * | 10/1997 | Hoopman et al. .................... 451/528 |

OTHER PUBLICATIONS

Andersson, M. et al., "A new all–ceramic crown," *Acta Odontol. Scand.*, vol. 51, pp. 59–64 (1993).
Ebbing, D., *General Chemistry*, pp. 877–881 (1993).
Edris, A. Al et al., "SEM evaluation of etch patterns by three etchants on three porcelains," *J. Prosthet. Dent.*, vol. 64, pp. 734–739 (1990).
Kern, M. et al., "Sandblasting and silica coating of a glass–infiltrated alumina ceramic: volume loss, morphology, and changes in the surface composition," *J. Prosthet. Dent.*, vol. 71, pp. 453–461 (1994).
Petzow, G., *Metallographic Etching*, pp. 91–94 (Engl. trans., 1978).
Sadoun, M. et al., "Bonding of resin cements to an aluminous ceramic: A new surface treatment," *Dent. Mater.*, vol. 10, pp. 185–189 (1994).
Thurmond, J. et al., "Effect of porcelain surface treatments on bond strengths of composite resin bonded to porcelain," *J. Prosthet. Dent.*, vol. 72, pp. 355–359 (1994).
Zeng, K. et al., "Flexure tests on dental ceramics," *Int. J. Prosthodont.*, vol. 9, pp. 434–439 (1996).

\* cited by examiner

Primary Examiner—Randy Gulakowski
Assistant Examiner—Jiri Smetana
(74) Attorney, Agent, or Firm—John H. Runnels

(57) ABSTRACT

A thermochemical process is disclosed that readily produces significantly roughened surfaces on densely sintered alumina. The alumina is reacted with cryolite ($Na_3AlF_6$) at a temperature of 300° C.–2075° C. for a time sufficient to produce the desired degree of roughness. This treatment causes controlled dissolution of alumina, controlled cavitation of grain boundaries, and formation of a thin film-reaction product. The resulting surface irregularities enhance subsequent micromechanical or chemical bonding of the densely sintered alumina component. The resulting roughened alumina components have numerous uses in the dental restorative and orthodontic fields, including orthodontic brackets, crowns, onlays, inlays, veneers, and the like. The technique is readily adapted to be used in either a dental office or a laboratory environment.

18 Claims, No Drawings

ETCHING ALUMINA CERAMICS

The benefit of the May 1, 1998 filing date of provisional application nnnnn (which was a conversion of nonprovisional application 09/071,333) is claimed under 35 U.S.C. § 119(e).

This invention pertains to ceramic materials used in restorative dentistry, electronics, and semiconductors, and to techniques for roughening the surfaces of such materials.

The three most commonly-used types of all-ceramic matrices in restorative dental work are densely sintered alumina, glass-infiltrated alumina ceramic, and leucite-reinforced porcelain. Densely sintered alumina ($Al_2O_3$) has been reported to be the strongest of the three. See K. Zeng et al., "Flexure tests on dental ceramics," *Int. J. Prosthodont.*, vol. 9, pp. 434–439 (1996). Densely sintered alumina is a popular restorative material due to its high strength and aesthetic appeal. The intaglio and outer surfaces of dental restorations (crowns, inlays, onlays, veneers, and the like) and of dental appliances (such as orthodontic brackets) made of densely sintered alumina are relatively smooth, however, making it difficult to bond them securely.

It is important to achieve a strong bond between, for example, a ceramic crown and the underlying tooth to permit the crown-tooth combination to withstand high load forces without failing. The strength of the bond between a resin cement and a ceramic surface depends largely on the presence of a rough ceramic interface that allows mechanical locking of bonding agents and resin cements into surface irregularities. Such rough surfaces are easily obtained in conventional glass based porcelains (e.g., feldspathic porcelain or leucite-reinforced feldspathic porcelain), by chemical etching of the ceramic surface with hydrofluoric acid, by air abrasion, or by a combination of the two techniques. See A. Al Edris et al., "SEM evaluation of etch patterns by three etchants on three porcelains," *J. Prosthet. Dent.*, vol. 64, pp. 734–739 (1990); and J. Thurmond et al., "Effect of porcelain surface treatments on bond strengths of composite resin bonded to porcelain," *J. Prosthet. Dent.*, vol. 72, pp. 355–359 (1994).

However, densely sintered or glass-infiltrated aluminas are not affected by such treatments: They are chemically inert to most chemical treatments, and they are too hard to be roughened by air abrasion. Two alumina etching processes from the metallographic literature have been reported in the dental literature: (1) thermal etching in air or other gasses, and (2) etching with hot or boiling hydrofluoric, sulfuric, or phosphoric acid. See pp. 91–94 in G. Petzow, *Metallographic Etching* (Engl. trans., 1978). These prior techniques produce only a limited degree of roughness, and in particular do not produce sufficient roughness to allow the effective retention of alumina restorations by cements. Other processes described in the dental literature are (1) sintering fine-grained refractory powder to the surface of a glass-infiltrated alumina ceramic, and (2) sandblasting and silica coating of glass-infiltrated alumina. See M. Sadoun et al., "Bonding of resin cements to an aluminous ceramic: A new surface treatment," *Dent. Mater.*, vol. 10, pp. 185–189 (1994); and M. Kern et al., "Sandblasting and silica coating of a glass-infiltrated alumina ceramic: Volume loss, morphology, and changes in the surface composition," *J. Prosthet. Dent.*, vol. 71, pp. 453–461 (1994).

Alumina is soluble in molten cryolite ($Na_3AlF_6$), a property that is used in the aluminum industry in the electrolytic production of aluminum metal. See, e.g., D. Ebbing, *General Chemistry*, pp. 877–881 (1993).

There is a continuing unfilled need for a method to rapidly and efficiently etch the surface of densely sintered alumina.

We have discovered a thermochemical process that readily produces roughened surfaces on densely sintered alumina. Alumina is reacted with cryolite at a temperature of 300° C.–2075° C., preferably between about 1000° C. and about 1030° C., most preferably about 1025° C.; for a time sufficient to produce the desired degree of roughness. This treatment causes controlled dissolution of alumina, controlled cavitation of grain boundaries, and formation of a thin film-reaction product. The resulting surface irregularities enhance subsequent micromechanical or chemical bonding of the densely sintered alumina component.

Without wishing to be bound by this theory, it is possible that the high pH of cryolite enhances the solubility of the alumina. Reaction of the two at a suitable combination of temperature and time causes the controlled dissolution of small pockets of alumina from the surface, producing a roughened surface.

The resulting roughened alumina components have numerous uses in the dental restorative and orthodontic fields, including orthodontic brackets, crowns, onlays, inlays, veneers, and the like. The technique is readily adapted to be used in a dental office, an industrial setting, or a laboratory environment.

The properties of densely sintered alumina treated in this manner were tested by two techniques. The first was to use scanning electron microscopy to examine changes in surface appearance. The novel process was used to treat the inner surface of a Procera AllCeram™ coping, which is a densely sintered alumina restoration product. See M. Andersson et al., "A new all-ceramic crown," *Acta Odoniol. Scand.*, vol. 51, pp. 59–64 (1993). Scanning electron microscopy revealed significant changes in the surface appearance after the application of the process on these specimens.

The second method compared the bonding strength of a treated surface to that of a comparable untreated surface. Untreated specimens and treated specimens were bonded to composite resin materials with dental bonding agents. This study included six densely sintered alumina samples, three of which were treated with cryolite by the novel technique, and three of which were left untreated. All six samples began as essentially identical, commercially-available orthodontic brackets purchased from the same manufacturer. Because the original surfaces of the brackets were irregular, those surfaces were ground until no irregularities were visible on the surfaces. Due to their small size, all samples were enveloped in resin blocks. All samples were trimmed on a model trimmer until no surface irregularities were apparent, and no foreign materials were visible. The samples were then smoothed with 600 grit sandpaper. The samples were placed in a furnace until the resin was eliminated (600° C. for 60 min.) The samples were measured (length and width).

Until this point, all six samples were treated identically. The three experimental samples were then treated with cryolite. A preferred method of applying the cryolite is the "salt and pepper" technique. The tip of a brush was dipped in water, and then touched gently onto cryolite powder. The adhering cryolite powder was dabbed onto the alumina surface, and the process was repeated several times to produce a thin layer (on the order of a few tenths of a millimeter or less, e.g., 0.1 to 0.5 mm). Alternatively, the cryolite could be applied to the alumina surface directly as a powder, as a paste (perhaps in glycerin), in solution, or as a spray.

The three experimental samples were placed in a furnace at 1025° C. for 30 minutes. Following removal from the furnace and cooling to room temperature, the three experimental samples were cleaned in an ultrasonic cleaner for 30 minutes to remove non-adherent cryolite from the surface.

All six samples were then cleaned with isopropanol. Dental adhesive (Scotchbond MP™, 3M Innovations) was applied to their surfaces, and the adhesive was light-cured (Optilux™ 500, Kerr), according to the manufacturer's recommendations for 10 sec. All samples were then attached to an uncured composite resin material (Z-100™, 3M Innovations), which was embedded in a resin block, and light-cured for 2 minutes.

The samples were then tested in an Instron™ machine. Force was applied between the sample and the adhesive in a direct shear mode until debonding occurred. The shear bond strength was then calculated as the ratio of (a) the applied force upon debonding failure to (b) the sample surface area. The results are summarized in Table 1.

TABLE 1

| Sample Number | Length (mm) | Width (mm) | Surface Area (mm$^2$) | Force to Failure (N) | Shear Bond Strength (MPa) |
|---|---|---|---|---|---|
| 1 (untreated) | 3.56 | 3.26 | 11.6 | 61.2[1] | 5.28 |
| 2 (untreated) | 3.60 | 3.36 | 12.1 | 11.3 | 0.93 |
| 3 (treated) | 3.34 | 3.23 | 10.8 | 171.5 | 15.90 |
| 4 (untreated) | 3.56 | 3.07 | 10.9 | 0[2] | 0 |
| 5 (treated) | 3.37 | 3.23 | 10.9 | 98.0[3] | 9.00 |
| 6 (treated) | 3.36 | 3.35 | 11.3 | 173.5 | 15.41 |

Notes to Table 1:
(1) All samples possessed undercuts. Sample 1 was slightly locked in the resin, which may explain the unusually high apparent bond strength for this sample.
(2) Sample 4 debonded before substantial force was applied.
(3) Sample 5 did not have the same "frosty" appearance as did the other two treated samples, which may indicate that too little cryolite was used in that treatment, explaining the relatively low bond strength for this sample.

The mean bond strength of the untreated group was 2.07 MPa (SD=2.82). The mean bond strength of the treated group was 13.44 MPa (SD=3.85). The average bond strength of the treated surfaces was significantly ($p<0.017$) higher than that of the untreated surfaces.

Applications in which the etched alumina of the present invention will be useful include, among others, dental applications (e.g., bonding crowns or other materials to enamel); and electronics or semiconductor applications (e.g., bonding alumina ceramics to other components of a circuit).

The complete disclosures of all references cited in this specification are hereby incorporated by reference. In the event of an otherwise irreconcilable conflict, however, the present specification shall control.

We claim:

1. A process for etching a surface of densely sintered alumina, comprising reacting the surface with cryolite at a temperature between about 300° C. and about 2075 ° C. until a desired degree of roughening of the surface has occurred.

2. The etched alumina produced by the process of claim 1.

3. A process as recited in claim 1, wherein the alumina comprises a dental restoration.

4. The etched dental restoration produced by the process of claim 3.

5. A process as recited in claim 1, wherein said reacting occurs at a temperature between about 1000° C. and about 1030° C.

6. The etched alumina produced by the process of claim 5.

7. A process as recited in claim 1, wherein said reacting occurs at a temperature of about 1025° C.

8. The etched alumina produced by the process of claim 7.

9. A process as recited in claim 1, wherein the cryolite is applied to the surface of the alumina in a layer between about 0.1 and about 0.5 millimeter thick.

10. The etched alumina produced by the process of claim 9.

11. A process as recited in claim 9, wherein the cryolite is applied to the surface of the alumina by successive applications with a brush whose tip is coated with cryolite powder.

12. The etched alumina produced by the process of claim 11.

13. A process as recited in claim 11, wherein said reacting occurs at a temperature between about 1000° C. and about 1030° C.

14. The etched alumina produced by the process of claim 13.

15. A process as recited in claim 11, wherein said reacting occurs at a temperature of about 1025° C.

16. The etched alumina produced by the process of claim 15.

17. A process as recited in claim 1, additionally comprising the step of removing unreacted cryolite from the etched alumina surface by ultrasound.

18. The etched alumina produced by the process of claim 17.

* * * * *